United States Patent [19]

Austin

[11] Patent Number: 5,659,122

[45] Date of Patent: *Aug. 19, 1997

[54] ENHANCED EXPRESSION IN PLANTS USING NON-TRANSLATED LEADER SEQUENCES

[75] Inventor: Glenn Douglas Austin, St. Peters, Mo.

[73] Assignee: Monsanto Company, St. Louis, Mo.

[*] Notice: The term of this patent shall not extend beyond the expiration date of Pat. No. 5,362,865.

[21] Appl. No.: 280,263

[22] Filed: Jul. 25, 1994

Related U.S. Application Data

[63] Continuation of Ser. No. 117,374, Sep. 2, 1993, Pat. No. 5,362,865.

[51] Int. Cl.⁶ .............. A01H 5/00; C12N 15/29; C12N 15/82
[52] U.S. Cl. .............. 800/205; 536/24.1; 536/24.5; 435/69.8
[58] Field of Search .............. 800/205; 536/24.1, 536/24.5; 435/69.8

[56] References Cited

U.S. PATENT DOCUMENTS 5,187,267  2/1993  Comai et al. .............. 536/23.1
5,362,865  11/1994  Austin .............. 536/24.1

FOREIGN PATENT DOCUMENTS 0 418 695 A1  9/1990  European Pat. Off. ........ C12N 15/82
90/02189  3/1990  WIPO .............. C12N 15/82

OTHER PUBLICATIONS

Kay et al., Science (1987) 236:1299–1302.
Leon et al., Plant Physiol. (1991) 95:968–972.
Pitto et al. 1992. Plant Phsiol. 100(4): 1827–1833.
Winter et al. 1988. Mol. Gen. Genet. 211(2): 315–319.
Czarnecka et al. 1988. Mol. Cell. Biol. 8(3): 1113–1122.
Callis et al. 1988. Plant Physiol. 88: 965–968.
Gallie et al. 1987. Nucl. Acids Res. 15(21): 8693–8711.
Schoffl et al. 1989. Mol. Gen. Genet. 217(2–3): 246–253.
Raschke et al. 1988. J. Mol. Biol. 199(3): 549–557.

*Primary Examiner*—David T. Fox
*Attorney, Agent, or Firm*—Janelle D. Strode; Dennis R. Hoerner, Jr.; Richard H. Shear

[57] ABSTRACT

This invention provides DNA molecules which comprise 5' non-translated leader sequences derived from genes coding for heat shock proteins that enhance gene expression in plants when present in a chimeric gene. Plant cells and plants containing same are also provided herewith. Further provided is a method for enhancing gene expression in plants.

6 Claims, 10 Drawing Sheets

Petunia HSP70-Fragment 1

5' ACACAGAAAAATTTGCTACATTGTTTCACAAACTTCAAATATTATTCATTTATTT 3'   SEQ ID NO.1
3' TGTGTCTTTTTAAACGATGTAACAAAGTGTTTGAAGTTTATAATAAGTAAATAAACAGTC 5'   SEQ ID NO.2

Petunia HSP70 -Fragment 2

5' GTCAGCTTTCAAACTCTTTGTTTCTTGTTTGTTGATTGAGAATAC 3'   SEQ ID NO.3
3'         GAAAGTTTGAGAAACAAAGAACAAACAACTAACTCTTATGGTAC 5'   SEQ ID NO.4

Petunia HSP70-Fragment 1
5' ACACAGAAAAATTGCTACATTGTTCACAAACTTCAAATATTATTCATTTATT 3'   SEQ ID NO.1
3' TGTGTCTTTTTAACGATGTAACAAGTGTTGAAGTTTATAATAAGTAAATAA 5'    SEQ ID NO.2

Petunia HSP70 -Fragment 2
5' GTCAGCTTTCAAACTCTTGTTTCTTGTTCTTGTTGTTGATTGAGAATAC 3'      SEQ ID NO.3
3' GAAAGTTTGAGAACAAAGAACAAGAACAACTAACTCTTATGGTAC 5'          SEQ ID NO.4

FIG.1

Soybean HSP17.9
5' ACACAGAAACATTCCGAAAAACAAATCCCAGTATCAAAATTCTCTCTCTTTTTTCATATATTCCGCAAAGAC 3'   SEQ ID NO.5
3' TGTGTCTTTGTAAGGCTTTTTGTTTTTAGGGTCATAGTTTTAAGAAGAGAAAAAAGTATATAAGGCGTTTCTGGTAC 5'   SEQ ID NO.6

FIG.2

Maize HSP70 — Fragment 1

5' ACACTCTCTCGCCTGAGAAAAAAATCCACGAACCAATTCTCAGCAACCAGCAGCACG 3'  SEQ ID NO.7
3' TGTGAGAGAGCGGACTCTTTTTTTTAGGTGCTTGGTTAAGAGTCGTTGGTCGTCGTGCTGGAC 5'  SEQ ID NO.8

Maize HSP70 — Fragment 2

5' ACCTGTGAGGGTTCGAAGGAAGTAGCAGTGTTTTTGTTCCTAGAGGAAGAGC 3'  SEQ ID NO.9
3'     ACTCCCAAGCTTCCTTCATCGTCACAAAAACAAGGATCTCCTTCTCGGTAC 5'  SEQ ID NO.10

FIG.3

AMV

5' ACACGTTTTTATTTTAATTTTCTTCAAATACTTCCATC 3'  SEQ ID NO.11
3' TGTGCAAAAATAAAAATTAAAAGAAGTTTATGAAGGTAGGTAC 5'  SEQ ID NO.12

FIG.4

TMV
5' ACACGTATTTTACAACAATTACCAACAACAAACAACAACATTACAATTACTATTACAATTACAC 3'  SEQ ID NO.13
3' TGTGCATAAAAATGTTGTTAATGGTTGTTGTTTGTTGTTGTAATGATAAATGTTAATGTGGTAC 5'  SEQ ID NO.14

FIG.5

AMV-B
5' ACACGTTTTATTTTAATTTCTTTCAATAAGAAGTTTATGAAGGTATCCATA 3'  SEQ ID NO.15
3' TGTGCAAAATAAAAATTAAAGAAAGTTATTCTTCAAATACTTCCATA 5'  SEQ ID NO.16

FIG.6

TMV-B
5' ACACGTATTTTACAACAATTACCAACAACAAACAACAACATTACAATTACTATTACAATTACAA 3'  SEQ ID NO.17
3' TGTGCATAAAAATGTTGTTAATGGTTGTTGTTTGTTGTTGTAATGTTAATGATAAATGTTCTAG 5'  SEQ ID NO.18

FIG.7

Soybean HSP17.9 - B

5' ACACAGAAACATTCGCAAAAACAAATCCCAGTATCAAAATTCTCTCTCTTTTTTCATATTCGCAAAGATTAAAAA 3'  SEQ ID NO. 19
3' TGTGTCTTTGTAAGCGTTTTGTTTAGGGTCATAGTTTTAAGAGAGAAAAAAGTATAAGCGTTTCTAATTTTTCTAG 5'  SEQ ID NO. 20

FIG. 8

Petunia HSP70 - B    Fragment 2B

5' GTCAGCTTCAAACTCTTGTTCTTGTTGTGATTGAGAATATTTAAAAA 3'  SEQ ID NO. 21
3' GAAAGTTTGAGAAACAAAGAACAAACAACTAACTCTTATAAATTTTTCTAG 5'  SEQ ID NO. 22

FIG. 9

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 55 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

ACACAGAAAA ATTTGCTACA TTGTTTCACA AACTTCAAAT ATTATTCATT TATTT    55

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

CTGACAAATA AATGAATAAT ATTGAAGTT TGTGAAACAA TGTAGCAAAT TTTCTGTGT    60

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

GTCAGCTTTC AAACTCTTTG TTTCTTGTTT GTTGATTGAG AATAC    45

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

CATGGTATTC TCAATCAACA AACAAGAAAC AAAGAGTTTG AAAG    44

( 2 ) INFORMATION FOR SEQ ID NO:5:

( i ) SEQUENCE CHARACTERISTICS:
  ( A ) LENGTH: 71 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:5:

```
ACACAGAAAC ATTCGCAAAA ACAAATCCC AGTATCAAAA TTCTTCTCTT TTTTTCATAT    60
TTCGCAAAGA C                                                       71
```

( 2 ) INFORMATION FOR SEQ ID NO:6:

( i ) SEQUENCE CHARACTERISTICS:
    ( A ) LENGTH: 75 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:6:

```
CATGGTCTTT GCGAAATATG AAAAAAGAG AAGAATTTTG ATACTGGGAT TTTGTTTTG     60
CGAATGTTTC TGTGT                                                   75
```

( 2 ) INFORMATION FOR SEQ ID NO:7:

( i ) SEQUENCE CHARACTERISTICS:
    ( A ) LENGTH: 59 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:7:

```
ACACTCTCTC GCCTGAGAAA AAAAATCCAC GAACCAATTT CTCAGCAACC AGCAGCACG    59
```

( 2 ) INFORMATION FOR SEQ ID NO:8:

( i ) SEQUENCE CHARACTERISTICS:
    ( A ) LENGTH: 64 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:8:

```
CAGGTCGTGC TGCTGGTTGC TGAGAAATTG GTTCGTGGAT TTTTTTCTC AGGCGAGAGA    60
GTGT                                                               64
```

( 2 ) INFORMATION FOR SEQ ID NO:9:

( i ) SEQUENCE CHARACTERISTICS:
    ( A ) LENGTH: 53 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:9:

```
ACCTGTGAGG GTTCGAAGGA AGTAGCAGTG TTTTTGTTC CTAGAGGAAG AGC           53
```

( 2 ) INFORMATION FOR SEQ ID NO:10:

( i ) SEQUENCE CHARACTERISTICS:
  ( A ) LENGTH: 52 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:10:

CATGGCTCTT CCTCTAGGAA CAAAAACAC TGCTACTTCC TTCGAACCCT CA                52

( 2 ) INFORMATION FOR SEQ ID NO:11:

( i ) SEQUENCE CHARACTERISTICS:
  ( A ) LENGTH: 40 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:11:

ACACGTTTTT ATTTTAATT TTCTTTCAAA TACTTCCATC                              40

( 2 ) INFORMATION FOR SEQ ID NO:12:

( i ) SEQUENCE CHARACTERISTICS:
  ( A ) LENGTH: 44 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:12:

CATGGATGGA AGTATTTGAA AGAAAATTAA AATAAAAAC GTGT                         44

( 2 ) INFORMATION FOR SEQ ID NO:13:

( i ) SEQUENCE CHARACTERISTICS:
  ( A ) LENGTH: 73 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:13:

ACACGTATTT TTACAACAAT TACCAACAAC AACAAACAAC AAACAACATT ACAATTACTA       60

TTTACAATTA CAC                                                         73

( 2 ) INFORMATION FOR SEQ ID NO:14:

( i ) SEQUENCE CHARACTERISTICS:
  ( A ) LENGTH: 77 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:14:

CATGGTGTAA TTGTAAATAG TAATTGTAAT GTTGTTTGTT GTTTGTTGTT GTTGGTAATT       60

GTTGTAAAAA TACGTGT                                                     77

( 2 ) INFORMATION FOR SEQ ID NO:15:

( i ) SEQUENCE CHARACTERISTICS:
       ( A ) LENGTH: 40 base pairs
       ( B ) TYPE: nucleic acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:15:

ACACGTTTTT ATTTTTAATT TTCTTTCAAA TACTTCCATA                40

( 2 ) INFORMATION FOR SEQ ID NO:16:

( i ) SEQUENCE CHARACTERISTICS:
       ( A ) LENGTH: 44 base pairs
       ( B ) TYPE: nucleic acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:16:

GATCTATGGA AGTATTTGAA AGAAAATTAA AAATAAAAAC GTGT           44

( 2 ) INFORMATION FOR SEQ ID NO:17:

( i ) SEQUENCE CHARACTERISTICS:
       ( A ) LENGTH: 73 base pairs
       ( B ) TYPE: nucleic acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:17:

ACACGTATTT TTACAACAAT TACCAACAAC AACAAACAAC AAACAACATT ACAATTACTA    60

TTTACAATTA CAA                                                       73

( 2 ) INFORMATION FOR SEQ ID NO:18:

( i ) SEQUENCE CHARACTERISTICS:
       ( A ) LENGTH: 77 base pairs
       ( B ) TYPE: nucleic acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:18:

GATCTTGTAA TTGTAAATAG TAATTGTAAT GTTGTTTGTT GTTGTTGTT GTTGGTAATT     60

GTTGTAAAAA TACGTGT                                                   77

( 2 ) INFORMATION FOR SEQ ID NO:19:

( i ) SEQUENCE CHARACTERISTICS:
       ( A ) LENGTH: 78 base pairs
       ( B ) TYPE: nucleic acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:19:

ACACAGAAAC ATTCGCAAAA ACAAAATCCC AGTATCAAAA TTCTTCTCTT TTTTCATAT     60

TTCGCAAAGA TTTAAAAA                                                  78

( 2 ) INFORMATION FOR SEQ ID NO:20:

(i) SEQUENCE CHARACTERISTICS:
    (A) LENGTH: 82 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:20:

```
GATCTTTTTA AATCTTTGCG AAATATGAAA AAAAGAGAAG AATTTTGATA CTGGGATTTT      60
GTTTTTGCGA ATGTTTCTGT GT                                              82
```

(2) INFORMATION FOR SEQ ID NO:21:

(i) SEQUENCE CHARACTERISTICS:
    (A) LENGTH: 52 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:21:

```
GTCAGCTTTC AAACTCTTTG TTTCTTGTTT GTTGATTGAG AATATTTAAA AA             52
```

(2) INFORMATION FOR SEQ ID NO:22:

(i) SEQUENCE CHARACTERISTICS:
    (A) LENGTH: 51 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:22:

```
GATCTTTTTA AATATTCTCA ATCAACAAAC AAGAAACAAA GAGTTTGAAA G              51
```

ENHANCED EXPRESSION IN PLANTS USING NON-TRANSLATED LEADER SEQUENCES

RELATED APPLICATIONS

This application is a continuation of application Ser. No. 08/117,374, filed Sep. 2, 1993, now U.S. Pat. No. 5,362,865.

FIELD OF THE INVENTION

The present invention is related to the genetic engineering of plants. In particular, the present invention relates to recombinant expression systems using non-translated leader sequences derived from heat shock proteins for the enhanced expression of proteins in plants.

BACKGROUND OF THE INVENTION

Recombinant genes for producing proteins in plants comprise in sequence the following operably linked elements: a promoter which functions in plants, a structural gene encoding the target protein, and a non-translated region which also functions in plants to cause the addition of polyadenylated nucleotides to the RNA sequence. Much scientific effort has been directed to the improvement of these recombinant plant genes in order to achieve the expression of larger amounts of the target protein.

One advantage of higher levels of expression is that fewer numbers of transgenic plants would need to be produced and screened in order to recover plants which produce agronomically significant quantities of the target protein. High level expression of the target protein often leads to plants which exhibit commercially important properties.

Improved recombinant plant genes have been generated by using stronger promoters, such as promoters from plant viruses. Further improvements in expression have been obtained in gene constructs by placing enhancer sequences 5' to the promoter. Still further improvements have been achieved, especially in monocot plants, by gene constructs which have introns in the non-translated leader positioned between the promoter and the structural gene coding sequence. For example, Callis et al. (1987) Genes and Development, Vol. 1, pp. 1183-1200, reported that the presence of alcohol dehydrogenase-1 (Adh-1) introns or Bronze-1 introns resulted in higher levels of expression. Dietrich et al. (1987) reported that the length of the 5' non-translated leader was important for gene expression in protoplasts. Mascarenkas et al. (1990) reported a 12-fold and 20-fold enhancement of CAT expression by use of the Adh-1 intron.

Expression of recombinant plant genes may also be improved by the optimization of the non-translated leader sequences. These leader sequences are by definition located at the 5' end of the mRNA and are untranslated. The leader sequence is further defined as that portion of the mRNA molecule which extends from the 5' CAP site to the AUG protein translation initiation codon. This region of the mRNA plays a critical role in translation initiation and in the regulation of gene expression. For most eukaryotic mRNAs, translation initiates with the binding of the CAP binding protein to the mRNA cap. This is then followed by the binding of several other translation factors, as well as the 43S ribosome pre-initiation complex. This complex travels down the mRNA molecule while scanning for a AUG initiation codon in an appropriate sequence context. Once this has been found and with the addition of the 60S ribosomal subunit, the complete 80S initiation complex initiates protein translation (Pain 1986; Moldave 1985; Kozak 1986). A second class of mRNAs have been identified which possess translation initiation features different from those described above. Translation from these mRNAs initiates in a CAP-independent manner and is believed to initiate with the ribosome binding to internal portions of the leader sequence (Sonenberg 1990; Carrington and Freed 1990; Jackson et al. 1990).

The efficiency of translation initiation is determined by features of the 5' mRNA leader sequence, and presumably this ultimately affects the levels of gene expression. By optimizing the leader sequence, levels of gene expression can be maximized. In plant cells most studies have investigated the use of plant virus leaders for their effects on plant gene expression (Gallie et al. 1987; Jobling and Gehrke 1987; Skuzeski et al. 1990). The most significant increases in gene expression have been reported using the Tobacco Mosaic Virus Omega (TMV) leader sequence. When compared with other viral leader sequences, such as the Alfalfa Mosaic Virus RNA 4 (AMV) leader, two to three fold improvements in the levels of gene expression have been observed using the TMV Omega leader sequence (Gallie et al. 1987; Skuzeski et al. 1990). Larger increases in gene expression have been observed when comparisons were made with an artificial non-native leader sequence. No consensus regulatory sequences have been identified within the TMV leader sequence.

Like the TMV leader sequence, most 5' untranslated leader sequences are very A,U rich and are predicted to lack any significant secondary structure. One of the early steps in translation initiation is the relaxing or unwinding of the secondary mRNA structure (Sonenberg 1990). Messenger RNA leader sequences with negligible secondary structure may not require this additional unwinding step and may therefore be more accessible to the translation initiation components. Introducing sequences which can form stable secondary structures reduces the level of gene expression (Kozak 1988; Pelletier and Sonenberg 1985). The ability of a leader sequence to interact with translational components may play a key role in affecting levels of subsequent gene expression.

In the search for leader sequences with improved properties, genes coding for heat shock proteins were scrutinized. Regulation of heat shock genes has been shown to occur at the transcriptional and translational level (Baumann et al. 1987; Kimpel and Key, 1985). Heat shock genes may be induced and expressed in response to hyperthermic stress (Key et al. 1981), as well as in response to other environmental conditions. During heat shock there is preferential translation of heat shock mRNAs (Storti et al. 1980). The translational control has been shown to be determined by the 5' untranslated leader sequence (McGarry and Lindquist 1985). A heat shock mRNA leader sequence operably linked to the mRNA of a non-heat shock gene would facilitate translation during heat shock conditions (Klemenz et al. 1985). The specific aspects of this regulation are not known. The heat shock mRNA 5' leader sequence may be more efficient at initiating translation, or may contain a particular structural feature that allows preferential translation during heat shock. Whatever the mechanism, the characteristics of the heat shock mRNA leader sequence may also provide an improvement to gene expression during non-heat shock conditions.

This invention makes a significant contribution to the art by providing non-translated leader sequences for use in genetic constructs which enhance gene expression in plants. The 5' non-translated leader sequences described herein provide for a significant increase in expression over other non-translated leader sequences which have been previously employed by those skilled in the art.

SUMMARY OF THE INVENTION

It is an object of the present invention to provide an isolated DNA molecule which comprises:

(a) a promoter which functions in plant cells to cause the production of an RNA sequence; which is operably linked to (b) a non-translated leader sequence derived from a heat shock protein, wherein said non-translated leader sequence is heterologous to said promoter; which is operably linked to (c) a structural DNA sequence, wherein said structural DNA seuqence is heterologous to said non-translated leader sequence; which is operably linked to (d) a 3' non-translated sequence that functions in plant cells to cause the termination of transcription and the addition of polyadenylated ribonucleotides to the 3' end of the transcribed mRNA sequence.

It is a further object of this invention to provide a method for enhancing gene expression in plants which comprises:

(a) transforming plant cells with a DNA molecule which comprises:
  (i) a promoter region which functions in plant cells to cause the production of an RNA sequence; which is operably linked to
  (ii) a non-translated leader sequence derived from a heat shock protein, wherein said non-translated leader sequence is heterologous to said promoter, which is operably linked to
  (iii) a structural DNA sequence, wnereinsaid structural DNA sequence is heterologous to said non-translated leader sequence; which is operably linked to
  (iv) a 3' non-translated DNA sequence which functions in plant cells to cause the termination of transcription and the addition of polyadenylated ribonucleotides to the 3' end of the transcribed mRNA sequence;

(b) selecting said plant cells which have been transformed;

(c) regenerating said plant cells to provide a differentiated plant; and (d) selecting a transformed plant which expresses said structural gene.

Yet another object of the present invention is to provide a transformed plant which contains a DNA molecule which comprises:

(a) a promoter which functions in plant cells to cause the production of an RNA sequence; which is operably linked to (b) a non-translated leader sequence derived from a heat shock protein, wherein said non-translated leader sequence is heterologous to said promoter; which is operably linked to (c) a structural DNA sequence, wherein said structurla DNA sequence is heterologous to said non-translated leader sequence; which is operably linked to (d) a 3' non-translated sequence that functions in plant cells to cause the termination of transcription and the addition of polyadenylated ribonucleotides to the 3' end of the transcribed mRNA sequence.

Other objects, aspects, and advantages of the present invention will be apparent to those skilled in the art from the following description, Example, and claims.

BRIEF DESCRIPTION OF THE DRAWINGS

FIG. 1 illustrates the petunia HSP70 leader sequence (SEQ ID NO.1, SEQ ID NO.2, SEQ ID NO.3, and SEQ ID NO.4).

FIG. 2 illustrates the soybean HSP17.9 leader sequence (SEQ ID NO.5 and SEQ ID NO.6).

FIG. 3 illustrates the maize HSP70 leader sequence (SEQ ID NO.7, SEQ ID NO.8, SEQ ID NO.9, and SEQ ID NO.10).

FIG. 4 illustrates the AMV leader sequence (SEQ ID NO.11 and SEQ ID NO.12).

FIG. 5 illustrates the TMV leader sequence (SEQ ID NO.13 and SEQ ID NO.14).

FIG. 6 illustrates the AMV-B leader sequence (SEQ ID NO.15 and SEQ ID NO.16).

FIG. 7 illustrates the TMV-B leader sequence (SEQ ID NO.17 and SEQ ID NO.18).

FIG. 8 illustrates the Soybean HSP17.9-B leader seuence (SEQ ID NO.19 and SEQ ID NO.20).

FIG. 9 illustrates the Petunia HSP70-B leader sequence (SEQ ID NO.21 and SEQ ID NO.22).

DETAILED DESCRIPTION OF THE INVENTION

Figure 10:
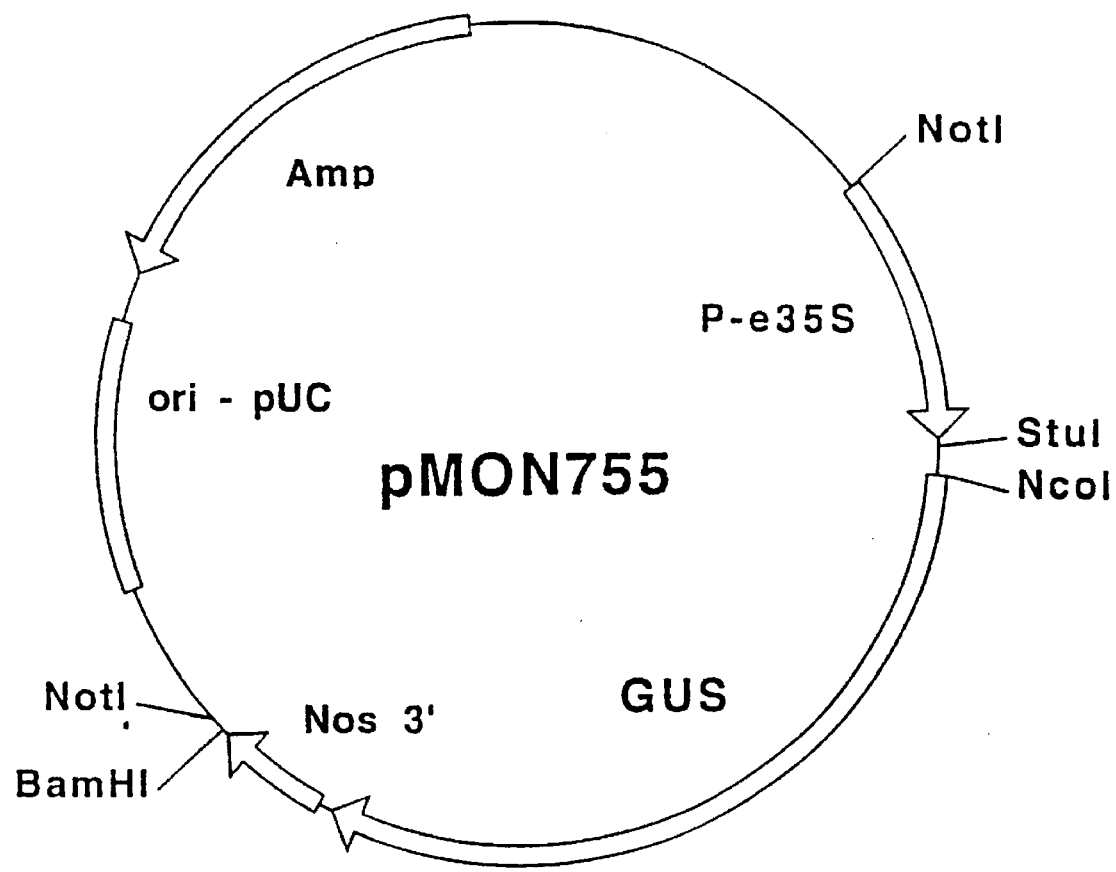
FIG. 10 illustrates pMON755.
Figure 11:
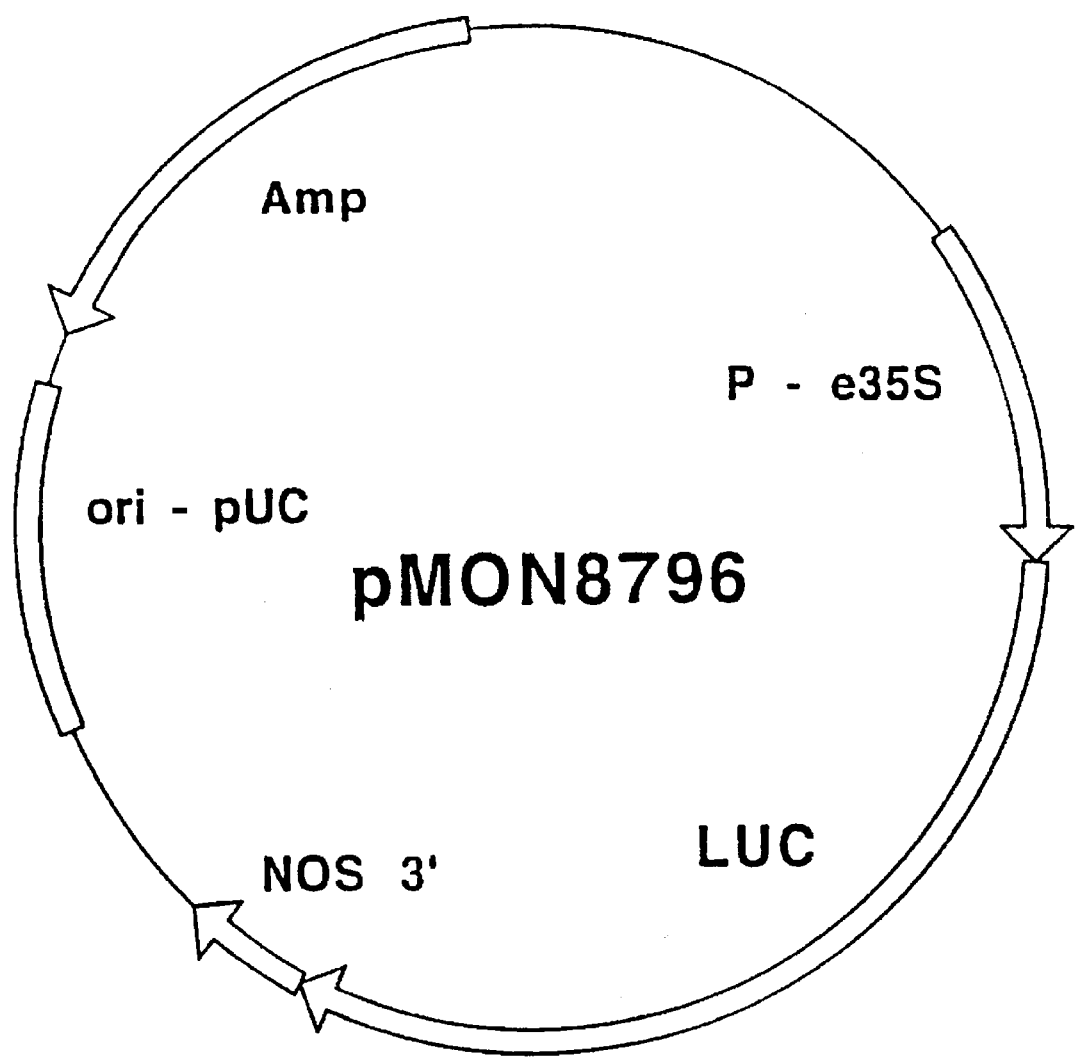
FIG. 11 illustrates pMON8796.
Figure 12:
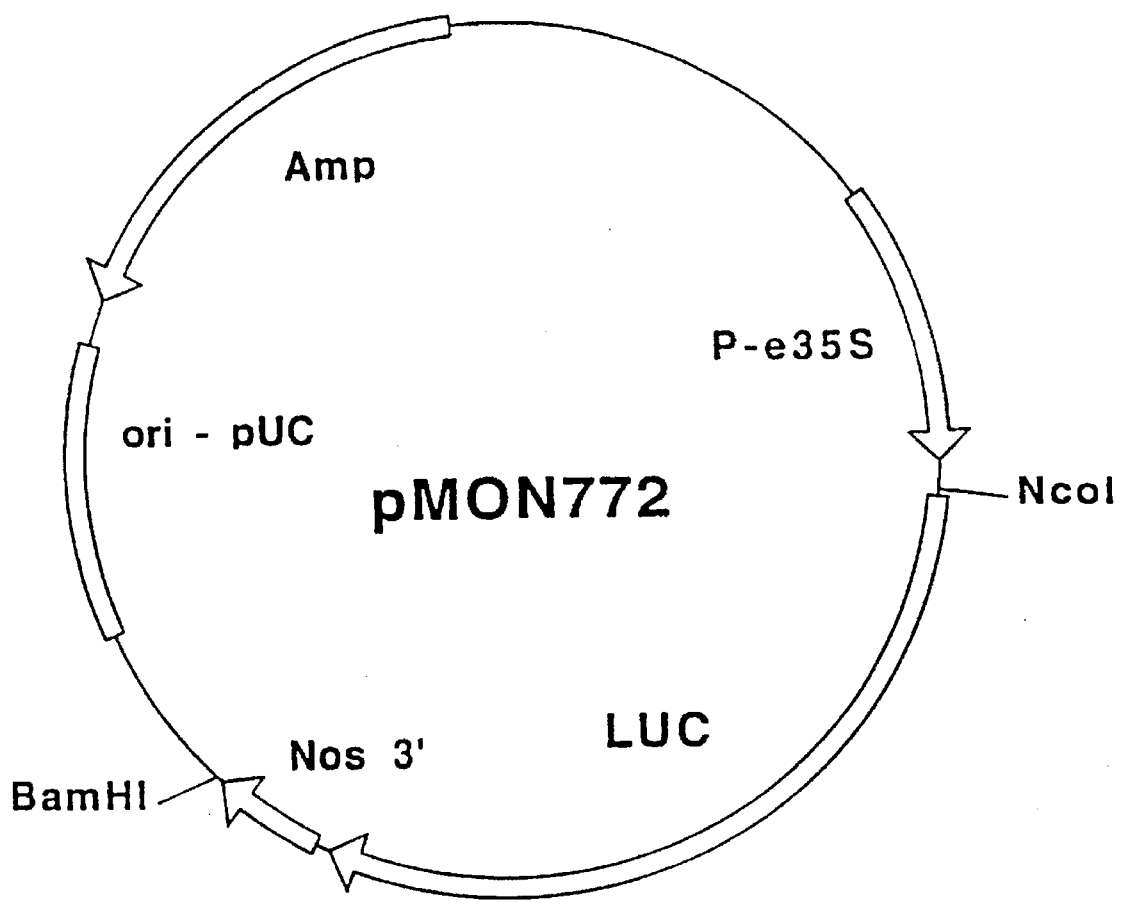
FIG. 12 illustrates pMON772.
Figure 13:
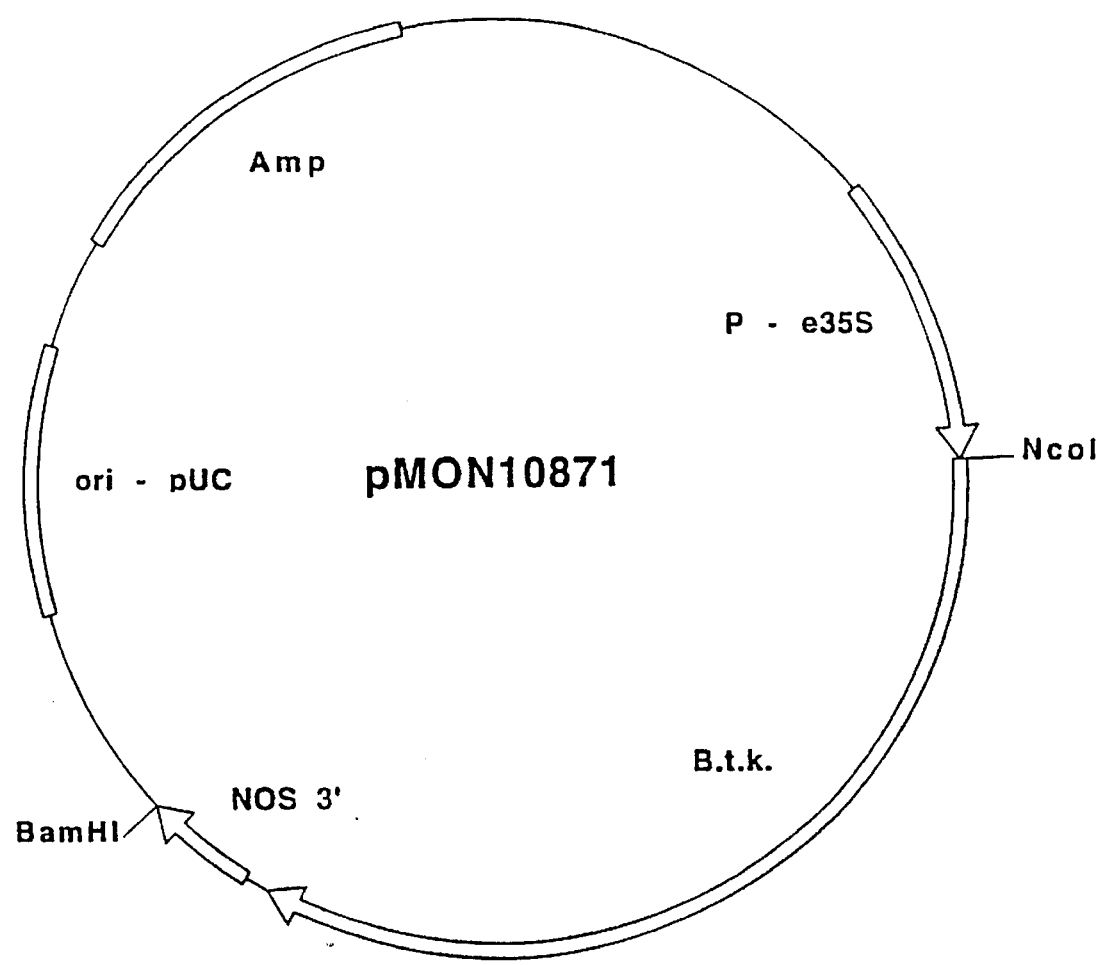
FIG. 13 illustrates pMON10871.
Figure 14:
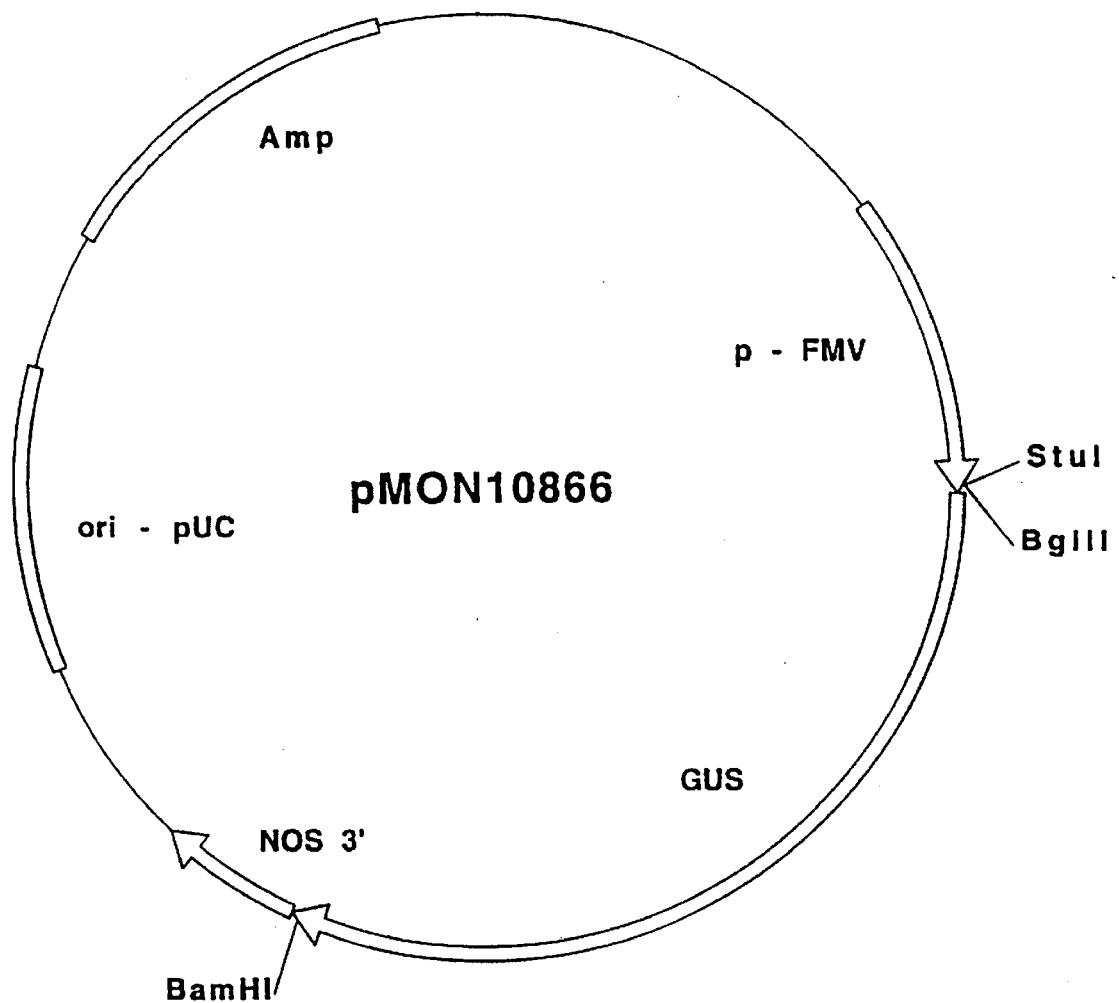
FIG. 14 illustrates pMON10086.
Figure 15:
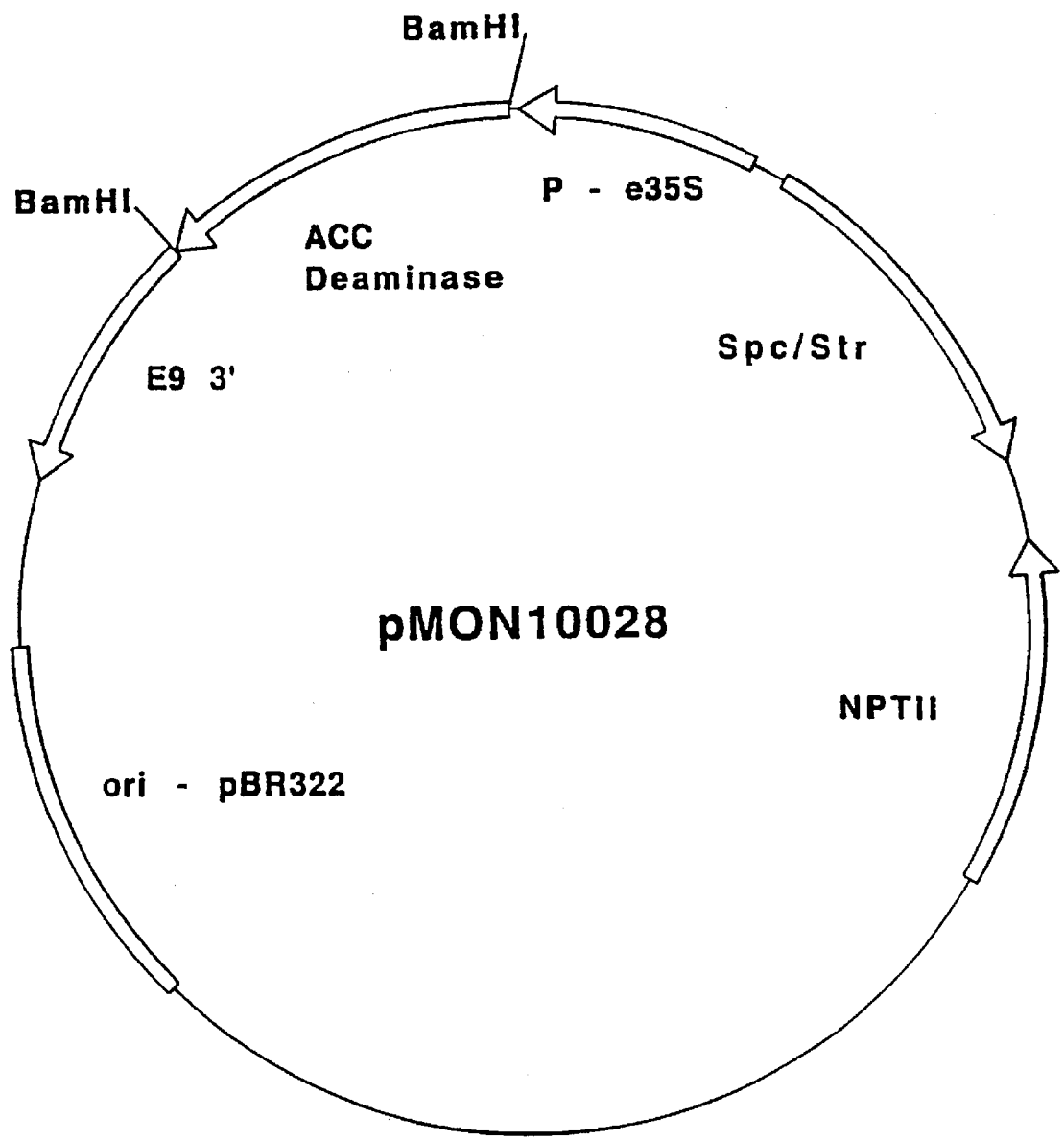
FIG. 15 illustrates pMON10028.

Enhanced gene expression in plants is herein provided by the use of 5' non-translated leader sequences derived from heat shock proteins in genetic constructs. Plant gene expression employing vectors containing same may be evaluated in order to determine whether or not said expression is in fact enhanced by the use of a heat shock 5' non-translated leader sequence during non-heat shock conditions.

Heat shock proteins are proteins which are induced in response to a particular stress-related event. The heat shock response is not limited to plants, and has been noted in organisms as diverse as Drosophila, *Escherichia coli*, *Saccharomyces cerevisiae*, and humans. The particular stress-related event is also not solely limited to an increase in temperature as the name "heat shock protein" would suggest. Other stress-related events which induce heat shock proteins include, for example, an exposure to ethanol, arsenite, heavy metals, amino acid analogues, glucose starvation, calcium ionophores, and a number of other treatments.

Heat shock proteins are typically designated as HSPX, wherein X is a number which reflects the molecular weight of the protein in question. Suitable heat shock proteins from which 5' non-translated leader sequences could be isolated include but are not limited to HSP70 from petunia, HSP17.3, 17.5, 17.9, 18.5, and 26 from soybean, and HSP18, 22, 27, 65, 68, 70, 72, 77, 78, 79, 85, and 87 from maize. Said 5' non-translated leader sequences are selected such that the leader sequences provide for enhanced expression in plants. In addition, those of skill in the art would recognize that certain optimizations of the 5' non-translated leader sequences disclosed herein may in fact be made such that the expression levels may be altered. These optimizations may involve changes in the nucleotide sequence of the leader such that a change in the secondary structure results therefrom. It is speculated that the secondary structure of the leader is required for the enhancement of expression; the specific nucleotide sequence of the leader is important insofar as the secondary structure is concerned. Therefore, the leader sequence may in fact tolerate modifications in the nucleotide sequence which do not result in changes in the secondary structure. These changes would not affect the resulting expression levels, and are in fact contemplated by the present invention.

Preferred for the practice of the present invention are those 5' non-translated leader sequences selected from the group consisting of petunia HSP 70, soybean HSP17.9 and the Maize HSP70.

The 5' non-translated leader sequences from plant heat shock genes have been shown to regulate gene expression during heat shock conditions. The mechanism for this selective or enhanced expression may in fact extend to non-heat shock conditions, thereby providing a means for selectively increasing plant gene expression. Several plant heat shock 5' non-translated leader sequences have been evaluated for their effect on plant gene expression during non-heat shock conditions. 5' non-translated leader sequences were tested in dicot and monocot species using both transient and stable plant transformation assays.

The 5' non-translated leader sequence may be isolated from a gene expressing a known heat shock protein by methods known to those of skill in the art, or alternatively, may be synthesized from a known sequence. In the practice of the instant invention, all leaders were generated as synthetic oligonucleotides and were tested with several different genes to show that the enhanced expression was general and not gene specific. Data demonstrating this is included in the Example.

Nucleic acid sequences which contain a 5' non-translated sequence may also be obtained by using the specific 5' non-translated sequences disclosed herein as probes. These obtained sequences could then be evaluated for enhanced expression in plants.

The nucleotide sequence of the 5' non-translated leader sequence may be modified at the 5' and 3' ends to facilitate cloning. This may be accomplished by site-directed mutagenesis, using the method described by Kunkel (1985), and may provide different restriction sites as needed. Various oligonucleotide primers may be used to modify the 5' and 3' ends. Multilinkers may be utilized, which facilitate ordered assembly of the heterologous DNA sequence. Sequencing of the respective 5' non-translated leader sequence may be performed by the method of Sanger and Coulson, Proc. Nat'l Acad. Sci. 74:5468-5467 (1977) using a Sequenase® product, according to the manufacturer's instructions.

Expression levels of the various constructs may be evaluated by comparing the level of expression with that obtained using a known leader sequence, such as, for example, those 5' non-translated leader sequences obtained from TMV-Omega and AMV as discussed previously, wherein the baseline of expression is that obtained using the known leader sequence. Furthermore, the instant invention embraces the additional feature that the enhanced expression of genes using the 5' non-translated leader sequences occurs during non-heat shock conditions.

The use of 5' non-translated leader sequences may result in overall expression levels which vary from gene to gene. This variability may in fact be due to a number of reasons including but not limited to the efficiency of expression of a particular gene. For example, the expression of a Bacillus thuringiensis toxin gene using the 5' non-translated leader sequences may be lower than the expression of an ACC deaminase gene using the same general construct as is taught by the instant invention. One postulated explanation for the cause of lower expression is the possible presence of fortuitous transcription processing sites, which could produce aberrant forms of the Bacillus thuringiensis mRNA transcript as is discussed in Koziel et al., WO 93/07278. These aberrantly processed transcripts may be non-functional in a plant, in terms of producing an insecticidal protein. Possible processing sites include polyadenylation sites, intron splicing sites, transcriptional termination signals, and transport signals. The fortuitous occurrence of such processing sites in a coding region might complicate the expression of that gene in transgenic hosts, which may include improper processing in plants.

A series of plasmids or vectors may be constructed, wherein the vectors would each contain a different heat shock 5' non-translated leader sequence fused to a particular reporter or structural gene. The level of reporter gene activity would then be measured and compared with the activity of vectors which contained previously described plant virus leader sequences such as the TMV and AMV leader sequences previously described. Two dicot heat shock 5' leader sequences, the petunia HSP70 (Winter et al. 1988) and soybean HSP17.9 (Raschke et al. 1988) leader sequences were shown to increase levels of gene expression in a dicot system. In addition, the maize HSP70 5' leader sequence was shown to increase levels of gene expression in maize cells (a monocot system) (pMON9508—Rochester et al. 1986).

Disclosed in the Example herein is the evaluation of three heat shock leaders in various constructs for their effect on plant gene expression. The 5' non-translated leader sequences employed were the petunia HSP70 (Winter et al. 1988), the soybean HSP17.9 (Raschke et al. 1988) and the maize HSP70 (pMON9508—Rochester et al. 1986) 5' non-translated leaders. Comparisons for effects on plant gene expression were made to the AMV and TMV plant viral leader sequences.

The 5' non-translated leader sequence for the soybean (Raschke et al. 1988) and maize (Rochester et al. 1986) heat shock mRNAs was derived using published information detailing the start of transcription and translation for each heat shock gene. The start of translation is known for the petunia HSP70 mRNA. However, the start of transcription has not been determined. A start site was therefore chosen (base 144—Winter et al. 1988) based on the putative TATA box (bases 108-115, Winter et al. 1988; Joshi 1987) and from preliminary, unpublished experiments performed in order to determine the transcriptional start site. The TMV and AMV viral leaders were also constructed using synthetic oligonucleotides which contained the consensus 5' and 3' sequences as represented in the Example below.

It is understood that the particular nucleotide and/or amino acid sequences disclosed herein are representative in the sense that equivalent genes or portions thereof may be obtained and/or generated pursuant to this disclosure. By equivalent it is meant that said gene or portion thereof would function in a manner substantially the same as the gene disclosed herein, and would provide a benefit or particular characteristic to a plant in substantially the same manner.

A structural DNA sequence encoding a particular gene of interest may be inserted into a plant transformation vector. A gene is defined as an element or combination of elements that are capable of being expressed in a cell, either alone or in combination with other elements. In general, a gene comprises (from the 5' to the 3' end): (1) a promoter region which may include a 5' non-translated leader sequence capable of functioning in plant cells; (2) a structural gene or structural DNA sequence which codes for the desired protein; and (3) a 3' non-translated region, which typically causes the termination of transcription and the polyadenylation of the 3' region of the RNA sequence. Each of these elements is operably linked to the adjacent element. A gene comprising the above elements may be inserted by standard recombinant DNA methods into a plant transformation vector. Some or all of the elements of the gene may be present, with additional or remaining elements added to the vector if necessary. Additionally, the plant transformation vector may be constructed with all of the elements present except for the structural gene, which may then be added at an appropriate time by known methods.

The segment of DNA referred to as the promoter is responsible for the regulation of the transcription of DNA into mRNA. A number of promoters which function in plant cells are known in the art and may be employed in the practice of the present invention. These promoters may be obtained from a variety of sources such as plants or plant viruses, and may include but are not limited to promoters isolated from the caulimovirus group such as the cauliflower mosaic virus 35S promoter (CaMV35S), the enhanced cauliflower mosaic virus 35S promoter (CaMVe35S), the figwort mosaic virus full-length transcript promoter (FMV), and the promoter isolated from the chlorophyll a/b binding protein as is known in the art. Other useful promoters include promoters which are capable of expressing the enzyme in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato would be useful.

Alternate promoters, such as the promoter from glutamine synthetase for expression in vascular tissues or promoters from epidermal cells, could be used to express the protein in certain cell types. The patatin promoter could be used to express the protein in the tuber. The particular promoter selected is preferably capable of causing sufficient expression of the structural gene to which it is operably linked to result in the production of a suitable amount of the respective protein, but not so much as to be detrimental to the cell in which it is expressed. The promoters selected should be capable of functioning in tissues including but not limited to epidermal, vascular, and mesophyll tissues. The actual choice of the promoter is not critical, as long as it has sufficient transcriptional activity to accomplish the expression of the structural gene.

The non-translated leader sequence can be derived from any suitable source and may be specifically modified to increase the translation of the mRNA. The 5' non-translated region may be obtained from the promoter selected to express the gene, the native leader sequence of the gene or coding region to be expressed, viral RNAs, suitable eucaryotic genes, or a synthetic gene sequence. Specifically, the 5' non-translated leader sequence may be heterologous to the promoter employed in the construct, for example, the non-translated leader sequence may be derived from an unrelated promoter as described. The present invention is not limited to the constructs presented in the following Example.

The structural DNA sequence which codes for the structural gene may be isolated from a particular source using methods known to those of skill in the art as discussed earlier in this section. Other modifications to this gene may also be made, including modifications to the 5' or 3' termini of the structural gene, such as, for example, the introduction of an initiation codon at the 5' end. Such structural genes may in fact be heterologous to the 5' non-translated leader sequence. Suitable structural genes which may be employed in the practice of the present invention include those structural genes selected from the group consisting of ACC deaminase, PLRV replicase, viral coat proteins, EPSP synthase or other genes conferring herbicide tolerance, selectable marker genes, genes affecting carbohydrates or oils, and genes affecting carotenoids or other nutritional components produced in plants. In addition, expression of antisense genes may also be employed, such as ACC synthase, or genes conferring nematode resistance.

The termination region or 3' non-translated region which is employed is one which will cause the termination of transcription and the addition of polyadenylated ribonucleotides to the 3' end of the transcribed mRNA sequence. The termination region or 3' non-translated region will be additionally one of convenience. The termination region may be native with the promoter region, native with the structural gene, or may be derived from another source, and preferably include a terminator and a sequence coding for polyadenylation. Suitable 3' non-translated regions of the chimeric plant gene include but are not limited to: (1) the 3' transcribed, non-translated regions containing the polyadenylate signal of Agrobacterium tumor-inducing (Ti) plasmid genes, such as the nopaline synthase (NOS) gene, (2) plant genes like the soybean 7S storage protein genes and the pea small subunit of the ribulose 1,5-bisphosphate carboxylase-oxygenase (ssRUBISCO) E9 gene and the like.

In developing the expression construct, the various components of the expression construct or fragments thereof will normally be inserted into a convenient cloning vector which is capable of replication in a bacterial host, such as E. coli. Numerous vectors exist that have been described in the literature. After each cloning, the vector may be isolated and subjected to further manipulation, such as restriction, insertion of new fragments, ligation, deletion, resection, insertion, in vitro mutagenesis, addition of polylinker fragments, and the like, in order to provide a vector which will meet a particular need. Once the construct is completed, it may then be transferred to an appropriate vector for further manipulation in accordance with the manner of transformation of the plant cell.

A variety of techniques are available for the introduction of the genetic material into or transformation of the plant cell host. However, the particular manner of introduction of the plant vector into the host is not critical to the practice of the present invention. Any method which provides for efficient transformation may be employed as is known and practiced by those of skill in the art. In addition to transformation using plant transformation vectors derived from the minor-inducing (Ti) or root-inducing (Ri) plasmids of Agrobacterium, alternative methods could be used to insert the DNA constructs of the present invention into plant cells. Such methods may include, for example, the use of liposomes, electroporation, chemicals that increase the free uptake of DNA, DNA delivery via microprojectile bombardment, microinjection, and transformation using viruses or pollen.

A plant transformation vector preferably includes all of the necessary elements for transformation of plant cells. Typical plant cloning vectors comprise selectable marker genes, scoreable marker genes, T-DNA borders, cloning sites, appropriate bacterial genes to facilitate the identification of transformants, broad host range replication and mobilization functions, and other elements as desired. The structural gene may be inserted into any suitable plant transformation vector for transformation into the desired plant species. Suitable plant transformation vectors include those derived from a Ti plasmid of *Agrobacterium tumefaciens*, in addition to those disclosed, for example, by Herrera-Estrella (1983), Bevan (1984), Klee (1985) and Fraley (1983).

Selectable marker genes may be used to select for those cells which have become transformed. Conveniently, the marker employed may be resistance to an antibiotic, such as kanamycin, G418, hygromycin, streptomycin, and the like. Other markers could be employed in addition to or in the alternative, such as, for example, a gene coding for herbicide tolerance such as tolerance to glyphosate, sulfonylurea, phosphinothricin, or bromoxynil. Additional means of selection could also be employed. The particular marker employed will be one which will allow for the selection of transformed cells as opposed to those cells which were not transformed. Depending on the number of different host species one or more markers may be employed, where different conditions of selection would be used to select the different host, and would be known to those of skill in the art.

Plant transformation vectors containing the 5' non-translated leader sequence which is operably linked to a structural gene may be used to transform plants of the Solanaceae family. An Agrobacterium-mediated transformation protocol is known to be effective in transforming members of the Solanaceae family. When an Agrobacterium-mediated transformation is used, the desired transformation vector is mobilized into a suitable Agrobacterium strain. The ABI Agrobacterium strain is described for exemplary purposes. The desired transformation vector is mobilized into an ABI Agrobacterium strain by the triparental mating system using the helper plasmid pRK2013 (Ditta et al. 1980). The binary ABI strain is the chloramphenicol resistant derivative of *Agrobacterium tumefaciens* A208 which carries the disarmed Ti plasmid pTiC58 (Koncz and Schell 1986). The Ti plasmid does not carry the T-DNA phytohormone genes and the strain is therefore unable to cause crown gall disease. The disarmed Ti plasmid provides the trfA gene functions required for autonomous replication of the vector after conjugation into the ABI strain. When the plant tissue is incubated with the ABI::transformation vector conjugate, the vector is transferred to the plant cells by the vir functions encoded by the disarmed pTiC58 plasmid. The pTiC58 Ti plasmid does not transfer to the plant cells, but remains in the Agrobacterium. Either single- or double-border transformation vectors can be delivered to the plant by Agrobacterium. Single border vectors open at the right T-DNA border region, and the entire vector sequence is inserted into the host plant chromosome. The right border is lost during transfer and integration. In a double border vector, DNA between the right and left borders is inserted into the plant chromosome, thereby delivering only the chimeric genes of interest to the chromosome. The remainder of the vector, and the border sequences are lost during the transfer and integration.

Transformation and regeneration protocols for members of the Solanaceae family are known in the art. After the tomato or potato plant has been transformed and after transformed callus has been identified, the transformed callus tissue is regenerated into whole plants. Any known method of regeneration of potato plants can be used in this invention.

For tomato, the transformation protocol described in McCormick et al. (1986) may generally be employed. The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soft. The regeneration of plants transformed by Agrobacterium from leaf explants can be achieved as described by Horsch et al., *Science* 227:1229–1231 (1985). In this procedure, transformants are grown in the presence of a selection agent and in a medium that induces the regeneration of shoots in the plant species being transformed as described by Fraley et al., *Proc. Nat'l. Acad. Sci.* U.S.A., 80:4803 (1983). This procedure typically produces shoots within 2 to 4 months and these transformant shoots are then transferred to an appropriate root-inducing medium containing the selective agent and an antibiotic to prevent bacterial growth. Transformant shoots that are rooted in the presence of the selective agent to form plantlets are then transplanted to soil or other media to allow the production of roots. These procedures vary depending on the particular plant species employed, such variations being well known in the art.

The invention also provides plant cells, the genome of which comprises an expression cassette comprising the 5' non-translated leader sequence of the present invention, wherein said 5' non-translated leader sequence functions in such a way as to provide enhanced expression of the structural gene to which the 5' non-translated leader sequence is operably linked. Whole plants comprising such cells will have the features or benefits provided by the expression of the structural gene which is operably linked to said 5' non-translated leader sequence. Such plants may be monocots or dicots, and may include but are not limited to plants belonging to families selected from the group consisting of Solanaceae, Graminae, Cucurbitaceae, Caricaceae, Dioscoreacea, Leguminosae, Compositae, and Chenopodiaceae.

A plant of the present invention containing the desired structural gene may be cultivated using methods known to those of skill in the art. A transformed plant of the present invention thus is capable of expressing the structural gene and exhibits the particular trait thereby. The presence of the particular structural gene or gene product in the transformed plant may be determined by any suitable method known to those of skill in the art. Included in these methods are Southern, Northern, and Western Blot techniques, ELISA, and various bioassays. The transformed plant capable of expressing the structural gene may then be assayed for the determination of the particular activity.

The following Example is provided to better elucidate the practice of the present invention and should not be interpreted in any way as to limit the scope of the present invention. Those skilled in the art will recognize that various modifications can be made to the methods, 5' non-translated leader sequences, and genes described herein while not departing from the spirit and scope of the present invention.

EXAMPLE

Each 5' leader oligonucleotide complementary pair was originally subcloned into the plasmid vector pMON755. The plasmid pMON755 is a pUC119 (Vieira and Messing 1987) based vector which contains the CaMV enhanced 35S promoter (e35S—Kay et al. 1987), the β-glucuronidase gene (GUS, pRAJ275, Clontech Laboratories, Inc.) and the nopaline synthase 3' termination sequence (NOS 3'—Fraley et al. 1983). In addition, pMON755 contains a Stu1 blunt end restriction enzyme site at the start of transcription from the CaMV promoter (Guilley et al. 1982) and a Nco1 site at the start of translation for the GUS gene (Jefferson et al. 1986). Synthetic oligonucleotides were designed as complimentary pairs which when annealed would generate a blunt 5' end, and would generate a 5' overhang at the 3' end which is compatible with and can be ligated to a DNA fragment restricted with Nco1. Each leader was also synthesized to contain the four nucleotides ACAC at the 5' end. These four nucleotides are the naturally occurring bases downstream of the start of CaMV transcription (Guilley et al. 1982) and were provided with each oligonucleotide to provide similar sequence context at the start of transcription for each leader construct. Similarly, a consensus sequence was used at the 3' end of the oligonucleotide to provide similar and near optimism sequence context at the start of translation (Kozak 1986).

Plasmid pMON755 was digested with Nco1 (Boehringer Manheim) and Stu1 (New England Biolabs) according to manufacturer directions. Complimentary synthetic oligonucleotide pairs were annealed and subcloned into pMON755. Each vector was identical except for the leader sequence used. The soybean HSP17.9 heat shock leader was constructed from one complimentary oligonucleotide pair. However, due to the long length and limitations of oligonucleotide synthesis, the petunia and maize HSP70 leaders were constructed from two pairs of complimentary oligonucleotides. For either the maize or petunia HSP leaders, two oligonucleotides were synthesized and annealed to generate Fragment 1. Similarily, two additional oligonucleotides were used to create Fragment 2. For cloning, Fragment 1 and Fragment 2 were ligated with previously digested pMON755 as described below. Ligations were performed using 25 pmol of each annealed oligonucleotide pair with 200 ngs of digested pMON755. Ligations were performed according to manufacturer's specifications (New England Biolabs). The *E. coli* host MM294 (Talmadge and Gilbert 1980) was rendered competent (Sambrook et al. 1989) and transformed with the ligation mix. Transformed cells were selected by plating the cells on LB media (Sambrook et al. 1989) containing 100 µg/ml carbenicillin (Sigma Chemical Company). Presence of the synthetic 5' leader was confirmed by restriction enzyme analysis. Leader sequences was verified from double stranded template DNA (prepared via Amorese mini-prep procedure from the Genesis 2000 DNA Analysis System, Application #8) using standard sequencing procedures (USB Sequenase® kit).

The constructs containing leader sequences were evaluated using a tobacco protoplast transient assay. TXD tobacco suspension cell protoplasts were electroporated with CsCl purified (Sambrook et al. 1989) plasmid DNA. Transformations were performed in triplicate and each transformation included an internal control plasmid. The control plasmid contained a different reporter gene and was used to correct for variability in the transformation and extraction procedures. For the GUS evaluations, the luciferase expression vector pMON8796 was used as the internal control. Other published plant luciferase vectors such as pDO432 (Ow et al. 1986) or pCaMVLN (Callis et al. 1987) could be used. pMON8796 is a pUC119 derivative (Vieira and Messing 1987) similar to pMON755 containing the e35S CaMV promoter, the luciferase (LUX) gene (De Wet et al. 1987) and the NOS 3'. For each transformation, 25 µg of plasmid DNA was used with 5 µg of the internal control plasmid.

TXD cells were grown in TXD media which contained 4.3 g/l Murashige and Skoog salts (Gibco), 3% sucrose, 0.2 g/l inositol, 0.13 g/l asparagine, 4 µg/ml of PCPA (p-chlorophenoxyacetic acid), 5 ng/ml of kinetin, 1.3 mg/l nicotinic acid, 0.25 mg/l thiamine, 0.25 mg/l pyridoxine HCL, and 0.25 mg/l calcium pantothenate at a pH of 5.8. Fifty mls of TXD cells were maintained in a 250 ml flask, in the dark at 25° C., shaking at 140 rpm. Cells were sub-cultured every 3–4 days by adding 9 mls of cells to 41 mls of fresh TXD media. For protoplast preparation, 16 mls of a 2 day old culture was added to 40 mls of fresh TXD medium. After approximately 24 hours cells were spun down in 50 ml sterile centrifuge tubes at 200×g for 5 minutes. The supernatant was removed and saved as conditioning media.

Forty mls of protoplast isolation media (7.35 g/l calcium chloride, 1 g/l sodium acetate, and 45 g/l mannitol pH 5.8), containing the following enzyme mixture 0.5% BSA (Sigma Fraction V), 40 µl β-mercaptoethanol, 0.5% cellulase 'RS' (Onazuka RS Yakult Honsha Co., LTD), 0.5% Rhozyme (Genecor HP-150), and 0.02% Y-23 pectolyase (Seishin Pharmaceutical Co., LTD) was then added to each tube, mixed with protoplasts using a wide bore pipette, and transferred to 100×25 mm petri dishes (10 ml/plate). The plates were parafilmed and incubated at 26°–28° C. on a rotary shaker at 50–60 rpm for one hour in the light. Digestion was monitored by observation through an inverted microscope. After digestion was complete the protoplasts were transferred back into 50 ml sterile centrifuge tubes using 10 ml pipettes with standard tips. The protoplasts were spun down at 200×g for 5 minutes. The supernatant discarded and the protoplasts gently resuspended in 20 mls protoplast isolation media. The protoplasts were spun down and then resuspended in 20 mls of electroporation buffer (EB—0.02 g/l $KH_2PO_4$, 0.115 g/l $Na_2HPO_4$, 7.5 g/l NaCl, and 36.4 g/l Mannitol pH 7.2). The protoplasts were counted using a hemocytometer and yields were determined. Protoplasts were spun down again and resuspended in EB to a density of $2\times10^6$ cells per ml and held on ice.

Electroporations were performed using a BioRad Gene Pulser® electroporation system (Gene Pulser and Capacitance Extender). Protoplasts (0.4 ml) were mixed with plasmid DNA (diluted to 0.4 ml with EB) and added to a 0.8 ml cuvette (BioRad 0.4 cm gap). The protoplasts and DNA were mixed by gently inverting the cuvette twice and then electroporated at 150 volts at a capacitance of 500 µFarads. The transformed protoplasts were placed on ice for 10 minutes then allowed to warm to room temperature for 10 minutes. Protoplasts were resuspended in 7 ml of TXD media containing 0.4M mannitol plus one-fifth volume of conditioning media (previously described) and transferred to 100×25 mm petri dishes. The protoplasts were then incubated in light at 26°–28° C. After 20–24 hours the protoplasts were collected by centrifugation and the media was removed. The pellet was resuspended in 250 µl extraction buffer (0.1M $KPO_4$ pH 7.8, 10 mM DTT, 1 mM NaEDTA, 5% glycerol). Cells were lysed for assay by freeze-thawing between dry ice and a 37° C. water bath. Cell debris was removed by centrifugation for 5 minutes at 16,000×g. GUS activity was determined from 5 µl of cell extract according to the methods of Jefferson et al. (1987) using 2 mM MUG in the previously described extraction buffer. Fluorescence was measured using a Hoescht DNA Fluorometer (Model TKO 100). A methylumbelliferone (Sigma) standard curve was generated using a 1 µm solution. GUS activity was calculated as pmol MU/minute/ml extract. To determine luciferase activity 5 µl of cell extract was added to 200 µl assay buffer (25 mM Tricine pH 7.8, 15 mM $MgCl_2$, 5 mM ATP, 0.5 mg/ml BSA) in a luminometer cuvette (Analytical Luminescence Laboratories). The cuvette was placed in a luminometer (Berthold Instruments Model LB9500) and reaction started with the addition of 100 μl 0.5 mm luciferin (Analytical Luminescence Laboratories). Peak light emission was measured over a 10 second interval. Five luciferase assays were perfomed per extract. Luciferase activity was calculated as the average relative light units/ml extract. For the comparison of different leader constructs expression results are presented as a ratio of activities for the experimental and control gene, i.e. GUS/LUX (pmol MU/min per average peak light units). Comparisons were made with the AMV leader, a leader which had previously been used to optimize gene expression in plants (Barton et al. 1987, Jobling and Gehrke 1987, McCabe et al. 1988). Results are shown in Table 1 below:

TABLE 1

Leader Effects on Transient Levels Of GUS Expression in Tobacco Protoplast Cells

| pMON | Leader | GUS/LUX | Relative Expression |
|---|---|---|---|
| 766 | AMV | 6.17 +/– 0.4 | 1.0 x |
| 769 | TMV | 15.4 +/– 1.2 | 2.5 x |
| 11711 | Soy HSP17.9 | 21.9 +/– 1.8 | 3.5 x |
| 11715 | Pet HSP70 | 22.3 +/– 3.1 | 3.6 x |

As indicated in Table 1 above, the level of gene expression using a heat shock leader sequence was greater than expression levels from the previously described viral leader sequences (Skuzeski et al. 1990). To show that this leader sequence effect was not specific for the GUS gene, a series of vectors were constructed which contained 5' leader sequence fusions to the luciferase, ACC deaminase, and the *Bacillus thuringinesis v. kurstaki* coding sequences (Ow et al. 1986, Klee et al. 1991, and Wong et al. 1992, respectively). To generate the luciferase vectors, the GUS coding sequence was replaced with the luciferase coding sequence from pMON772. The luciferase coding sequence was subcloned as a Nco1 to BamH1 fragment using standard digestion and ligation protocols. Similarily, the B.t.k. expression plasmids were constructed using a Nco1/BamH1 fragment isolated from pMON10871.

The ACC deaminase expression vectors were constructed as follows: Plasmid pMON 10866, which contains the P-FMV GUS NOS 3' gene, was digested with the restriction endonucleases Stu1 and Bgl2. New heat shock and control leader oligonucleotides were synthesized and subcloned into the digested pMON10866. These new leaders (FIGS. 6, 7, 8, and 9) are essentially identical to the previously described leaders except they contain modifications at their respective 3' overhangs to allow cloning into a Bgl2 restriction site. For the petunia HSP70 leader, only a new fragment 2 was synthesized (See FIG. 9); the previously described Fragment 1 (FIG. 1) was used here as well for the ACC deaminase cloning. The resulting plasmids were restricted with the endonucleases Bgl2 and BamH1. The ACC deaminase gene, isolated as a BamH1 fragment from pMON10028, was subcloned into the leader plasmids. The resulting plasmids contained the leader of interest fused to the ACC deaminase gene driven by the FMV promoter (Richins et al., 1987).

Tobacco protoplast transformations were performed with these leader luciferase vectors as previously described. An internal control GUS expression plasmid, pMON755, was included to correct for variations in the assay. Comparable GUS expression vectors such as pBI121 (Clontech Laboratories, Inc.) could also be used. Comparisons are again presented as LUX/GUS ratios and are included in Table 2 below:

TABLE 2

Leader Effects on Transient Levels Of Luciferase Expression in Tobacco Protoplast

| pMON | Leader | LUX/GUS | Relative Levels |
|---|---|---|---|
| 778 | AMV | 3.1 +/– 0.2 | 1.0 x |
| 781 | TMV | 8.5 +/– 0.5 | 2.7 x |
| 11718 | Soy HSP17.9 | 14.6 +/– 0.3 | 4.7 x |
| 11721 | Pet HSP70 | 12.6 +/– 0.8 | 4.1 x |

Levels of luciferase expression in tobacco protoplasts were greatest when using the heat shock leader sequences. The heat shock leader sequence constructs again gave levels of expression higher then the constructs which contained the plant viral leader sequences.

ACC deaminase evaluations were perfomed using the tobacco protoplast transient assay. Electroporated protoplasts were resuspended in 0.4 ml 0.1M Tris-HCl pH 7.8, 5 mM $Na_2EDTA$, 10 mM DTT and 10% glycerol. Cells were extracted by freeze-thaw as previously described. ACC deaminase activity was determined by quantitating levels of alpha-ketobutryate following incubation of the enzyme with the substrate ACC (Honma and Shimomura, 1978). 0.05 ml of tobacco cell extract was added to 0.05 ml of a solution containing 0.2M Tris-HCl pH 7.8 and 0.1M amino cyclopropane-1-carboxylic acid (ACC). This reaction mix was incubated at 37° C. for 30 minutes and then terminated with the addition of 0.9 ml of 0.56N HCl. To this solution was added 0.15 ml of 0.1% dinitrophenyl hydrazine in 2N HCl. The samples were then incubated for 15 minutes at 25° C. Following this period, 1.0 ml of 2N NaOH was added to the samples. Samples were allowed to sit for 15 minutes at 25° C. to allow the color to stabilize, then were measured for absorbance at O.D. $_{540}$ using a spectrophotometer. The luciferase vector pMON8796 was used as the internal control for the ACC deaminase electroporations. ACC deaminase transient assay results are presented as the average of 4 electroporations and are shown in Table 3 below:

TABLE 3

Leader Effects on Transient Levels Of ACC Deaminase Expression in Tobacco Protoplast

| pMON | 5' Leader | ACC Deaminase/LUX | Relative Levels |
|---|---|---|---|
| 18426 | AMV | 0.83 +/– 0.12 | 1.0 x |
| 18427 | TMV | 1.02 +/– 0.15 | 1.2 x |
| 18419 | Soy HSP17.9 | 1.45 +/– 0.33 | 1.8 x |
| 10116 | Pet HSP70 | 1.45 +/– 0.25 | 1.8 x |

Results from the luciferase and ACC deaminase experiments corroborate the earlier GUS findings, showing that the plant HSP 5' leader sequences can in fact increase plant gene expression to levels greater then that observed with previously described leader sequences. In addition, these results show that the heat shock leader sequence effect on plant gene expression extends beyond one particular coding sequence.

The tobacco transient assays was also used for evaluating the 5' leader effect on expression of the B.t.k. gene. The luciferase expressing plasmid pMON772 was included as an internal control. Luciferase expression levels were used to standardize loadings for western analysis of the B.t.k. protein. The electroporated protoplast were resuspended in extraction buffer (0.1M $KPO_4$, 5% glycerol, 1 mM EDTA, 10 mM DTT). One half of the resuspended cells were used for luciferase assays using the procedure previously described. To the remaining cell sample was added an equal volume of 2×SDS Loading buffer (125 mM Tris-HCL pH 7.0, 4% SDS, 20% glycerol, 10% β-mercapthoethanol, 4 mg/ml phenol red) followed by boiling for 5 minutes. Equivalent amounts of samples were loaded onto a 10% SDS-PAGE gel based on luciferase activities. Seperated proteins were then transferred to nitrocellulose membrane using a Hoeffer Transfer Appartus as per the manufacturers instructions. The membrane was incubated overnight at 4° C. in 5% dry milk/TBST (10 mM Tris, pH8, 150 mM NaCl, 0.1% Tween-20). To hybridize the membrane the incubations were done at room temperature with gentle agitation. The primary B.t.k. antibody was bound by incubating the membrane in a 1:2000 dilution of the rabbit serum in TBST for 18 hr. This was followed by three 10-min washes in TBST. The secondary reagent was bound by incubating the membrane with 5 μC of $^{125}$I-labelled protein G in 20 ml of TBST for 30 min. The membrane was washed three times for 10 min each with 0.3% Triton X-100 followed by three washings 0.1% Triton X-100 and then exposed to film. Levels of protein expression were determined using a densitometer. Results are as follows:

TABLE 4

Leader Effect On Transient Levels Of B.t. Expression In Tobacco Protoplast

| pMON | Leader | Relative Area | Relative Value |
|---|---|---|---|
| 11754 | AMV | 881.7 +/− 12.2 | 1.0 x |
| 11755 | TMV | 1194.0 +/− 2.8 | 1.4 x |
| 11756 | HSP17.9 | 1197.0 +/− 2.4 | 1.4 x |
| 11759 | Pet HSP70 | 933.7 +/− 31.9 | 1.1 x |

The results from the B.t.k. analysis did not reveal significant increases in expression as a result of the HSP leaders. However, expression was at least equivalent to the AMV and TMV leaders which have been described as preferred leaders for maximizing plant gene expression. Inability to significantly enhance B.t.k. expression may be a result of other constraints on B.t.k. expression separate from effects dependent upon the 5' leader. This may include fortuitous transcription processing sites, polyadenylation sites, intron splicing sites, transcriptional termination signals, and transport signals. The fortuitous occurrence of such processing sites in a coding region may in fact complicate the expression of that gene in transgenic hosts, which may include improper processing in plants.

In a similar manner a maize heat shock 5' leader was tested for its effect on maize gene expression. The maize HSP70 leader was subcloned as synthetic oligonucleotides in an identical fashion to the dicot leader sequences. The maize HSP70 leader was fused with the GUS and luciferase coding sequences. Leader sequence analysis was performed in a monocot transient assay system.

Maize BMS (Black Mexican Sweet—ATCC #54022) suspension cell protoplasts were transformed with the maize HSP70 leader constructs and with the previously described viral leader sequence constructs. Maize BMS cells were maintained and prepared for protoplast transformation as described by Fromm (Fromm et al. 1987) with the following exceptions. The BMS media used was as follows, MS salts (Gibco), 2 mg/L 2,4-D, 0.25 mg/L thiamine HCl, 1 mM asparagine, 20 g/L sucrose, 100 mg/L inositol, 1.3 mg/L nicotinic acid, 0.25 mg/L pyridoxine HCl and calcium pantothenate, pH 5.8. BMS lines were subcultured every other day by transfer of 25 mls suspended cells into 40 mls liquid media in 250 mls Erlenmeyer flasks. Lines were maintained in the dark or very low light, at 28° C., and at a shaker speed of 120–150 rpm. Protoplasts were isolated one day following subculturing (Fromm et al. 1987). One gram of fresh cell weight of BMS cells was digested with 10 mls of enzyme mixture. A protoplast concentration of 3×10$^6$ cells/ml was used for the electroporation. Electroporations were performed as described for tobacco. Following electroporation cells were placed on ice for 10 minutes then transferred to a 100×25 mm petri dish and allowed to sit at room temperature for 10 minutes. Eight mls of protoplast growth media (Fromm et al. 1987) were then added to the cells. Cells were incubated 20–24 hours at 26° in the dark. Cells were harvested and extracted as described for tobacco transformations with the following exceptions. The extraction buffer also included 1 mM phenylmethylsulfonylfluoride, 1 mM benzamidine, and 5 mM-aminocaproic acid. GUS assays were performed using 25 μl of extract. Luciferase assays were performed using 40 μl of extract with PEG-8000 (25 mg/ml) added to the luciferase assay buffer. As before, results are expressed as a ratio of experimental reporter gene levels to internal control reporter gene levels and are provided in Tables 5 and 6 below:

TABLE 5

Leader Effect On Transient Levels Of GUS Gene Expression In Maize BMS Cell Protoplast

| pMON | Leader | Average GUS/LUX | Relative Expression |
|---|---|---|---|
| 766 | AMV | 0.4 +/− 0.1 | 1.0 x |
| 769 | TMV | 0.4 +/− 0.1 | 1.0 x |
| 11714 | Mz HSP70 | 9.1 +/− 3.0 | 22.8 x |
| 11711 | Soy HSP17.9 | 14.0 +/− 0.1 | 35.0 x |
| 11715 | Pet HSP70 | 6.0 +/− 0.1 | 15.0 x |

TABLE 6

Leader Effect On Transient Levels Of Luciferase Gene Expression In Maize BMS Cell Protoplast

| pMON | Leader | Average LUX/GUS | Relative Expression |
|---|---|---|---|
| 778 | AMV | 6.9 +/− 1.1 | 1.0 x |
| 781 | TMV | 6.8 +/− 2.2 | 1.0 x |
| 11720 | Maize HSP70 | 86.2 +/− 2.5 | 12.5 x |
| 11718 | Soy HSP17.9 | 47.4 +/− 3.0 | 6.9 x |
| 11721 | Pet HSP70 | 21.3 +/− 4.5 | 3.0 x |

As observed in the dicot system, the use of a heat shock leader sequence in a monocot system greatly improved the level of monocot gene expression over that obtained with the plant virus leader sequences as shown in Tables 5 and 6 above.

All publications and patent applications mentioned in this specification are indicative of the level of skill of those skilled in the art to which this invention pertains.

From the foregoing, it will be seen that this invention is one well adapted to attain all the ends and objects hereinabove set forth together with advantages that are obvious and that are inherent to the invention. It will be understood that certain features and sub-combinations are of utility and can be employed without reference to other features and sub-combinations. This is contemplated by and is within the scope of the claims. Because many possible embodiments can be made of the invention without departing from the scope thereof, it is to be understood that all matter herein set forth or shown in the accompanying drawings is to be interpreted as illustrative and not in a limiting sense.

REFERENCES

Baumann, G., Raschke, E., Bevan, M., and Schöffl F. (1987). Functional analysis of sequences required for transcriptional activation of a soybean heat shock gone in transgenic tobacco plants. EMBO J. 6, 1161–1166.

Barton, K. A., Whiteley, H. R., and Yang, N. (1987). *Bacillus thuringiensis* δ-endotoxin expressed in transgenic *Nicotiana tabacum* provides resistance to lepidopteran insects. Plant Physiol. 85, 1103–1109.

Carrington, J. C., and Freed, D. D. (1990). Cap-independent enhancement of translation by a plant polyvirus 5' non-translated region. J. of Vir. 64, 1590–1597.

Czarnecka, E., Nagao, R. T., Key J. L., and Gurley, W. B. (1988). Characterization of Gmhsp26, a stress gone encoding a divergent heat shock protein of soybean: heavy-metal-induced inhibition of intron processing. Mol. and Cell. Biol. 8, 1113–1122.

Dietrich et al. J. Cell Biol., 105, 67 (1987).

De Wet, J. R., Wood K. V., DeLuca, M., Helinski, D. R., and Subramani S. (1987). Firefly luciferase gene: structure and expression in mammalian cells. Mol. and Cell. Biol. 7, 725–737.

Fraley, R. T., Rogers, S. G., Horsch, R. B., Sanders, P. R., Frick J. S., Adams S. P., Bittner, M. L., Brand L. A., Fink C. L., Fry J. S., Galluppi, G. R., Goldberg, S. B., Hoffmann, N. L., and Woo S. C. (1983). Expression of bacterial genes in plant cells. PNAS 80 4803–4807.

Fromm, M., Callis, J., Taylor, L., and Walbot, V. (1987). Electroporation of DNA and RNA into plant protoplast. Methods. Enzymol. 153, 351–366.

Gallie, D. R., Sleat, D. E., Watts, J. W., Turner, P. C., and Wilson, T. M. A. (1987). A comparison of eukaryotic viral 5' leader sequences as enhancers of mRNA expression in vivo. NAR 15, 8693–8711.

Guilley, H., Dudley, R. K., Jonard, G., Balazs, E., and Richards, K. E. (1982). Transcription of cauliflower mosaic virus DNA: detection of promoter sequences, and characterization of transcripts. Cell 30, 763–773.

Horsch, R. B., Fry, J. E., Hoffman, N. L., Eichholtz, D., Rogers, S. G., and Fraley, R. T. (1985). A simple and general method for transferring genes into plants. Science 227 1229–1231.

Horsch, R. B., and Klee, H. J. (1986). Rapid assay of foreign gene expression in leaf discs transformed by *Agrobacterium tumefaciens*: Role of T-DNA borders in the transfer process. PNAS 83 4428–4432.

Jackson, R. J., Howell, M. T., and Kaminski, A. (1990). The novel mechanism of initiation of picornavirus RNA translation. TIBS 15 December, 477–483.

Jefferson, R. A., Burgess S. M., and Hirsh, D. (1986). β-glucuronidase from *Escherichia coli* as a gene-fusion marker. PNAS 83, 8447–8451.

Jefferson, R. A., Kavanagh, T. A., and Bevan, M. W. (1987). GUS fusions: β-glucuronidase as a sensitive and versatile gene fusion marker in higher plants. EMBO 6, 3901–3907.

Jobling, S. A., and Gehrke, L. (1987). Enhanced translation of chimaeric messenger RNAs containing a plant viral untranslated leader sequence. Nature 325, 622–625.

Joshi, C. P. (1987). An inspection of the domain between putative TATA box and translation start site in 79 plant genes. NAR 15, 6643–6653.

Kay, R., Chan, A., Daly, M., and McPherson, J. (1987). Duplication of CaMV 35S promoter sequences creates a strong enhancer for plant genes. Science 236, 1299–1302.

Key, J. L., Lin C. Y., and Chen, Y. M. (1981). Heat shock proteins of higher plants. Proc. Natl. Acad. Sci. USA 78, 3526–3530.

Kimpel, J. A., and Key, J. L. (1985). Heat shock in plants. TIBS September, 353–357.

Klee, H. J., Hayford, M. B., Kretzmer, K. A., Barry, G. F. and Kishore, G. M. (1991). The Plant Cell 3, 1187–1193.

Klemenz, R., Hultmark, D., and Gehring, W. J. (1985). Selective translation of heat shock mRNA in *Drosophila melanogaster* depends on sequence information in the leader. EMBO J. 4, 2053–2060.

Kozak, M. (1986). Point mutations define a sequence flanking the AUG initiator codon that modulates translation by eukaryotic ribosomes. Cell 44, 283–292.

Kozak, M. (1988). Leader length and secondary structure modulate mRNA function under conditions of stress. Mol. and Cell. Biol. 8, 2737–2744.

Mascarenkas et al. Plant Mol. Biol., Vol. 15, pp. 913–920, (1990).

McCabe, D. E., Swain, W. F., Martinell, B. J., and Christou, P. (1988). Stable transformation of soybean (Glycine max) by particle acceleration. Bio/Technology 6 923–926.

McGarry, T. J., and LindQuist, S. (1985). The preferential translation of drosophila hsp70 mRNA requires sequences in the untranslated leader. Cell 42, 903–911.

Moldave, K, (1985). Eukaryotic protein synthesis. Ann. Rev. Biochem. 54, 1109–1149.

Ow, D. W., Wood, K. V., DeLuca, M., DeWet, J. R., Helsinki, D. R., Howell, S. H. (1986). Transient and stable expression of the firefly luciferase gene in plant cells and transgenic plants. Science 234, 856–859.

Pain, V. M. (1986). Initiation of protein synthesis in mammalian cells. Biochem. J. 235, 625–637.

Pelletier, J., and Sonenberg, N. (1985). Insertion mutagenesis to increase secondary structure within the 5' noncoding region of a eukaryotic mRNA reduces translational efficiency. Cell 40, 515–526.

Pierce, D. A., Mettler, I. J., Lachmansingh, L. M., Weck, E. A., and Mascarenhas, D. (1987). Effect of 35S leader modifications on promoter activity. Plant Gene Systems and Their Biology, Alan R. Liss, Inc., 301–310

Raschke, E., Baumann, G., and Schöffl, F. (1988). Nucleotide sequence analysis of soybean small heat shock protein genes belonging to two different multigene families. J. Mol. Biol. 199, 549–557.

Richins, R. D., Scholthof, H. B., and Shepard, R. J. (1987). Sequence of Figwort Mosaic Virus DNA. NAR 15, 8451–8466.

Rochester, D. E., Winter, J. A., and Shah. D. M. (1986). The structure and expression of maize genes encoding the major heat shock protein, hsp70. EMBO 5, 451–458.

Sambrook, J., Fritsch, E. F., and Maniatis, T. (1989). Molecular cloning: A laboratory manual—second edition. Cold Spring Harbor Laboratory Press, Cold Spring Harbor New York.

Skuzeski, J. M., Nichols, L. M., and Gesteland, R. F. (1990). Analysis of leaky vital translation termination codons in vivo by transient expression of improved β-glucuronidase vectors. Plant Mol. Biol. 15, 65–79

Sonenberg, N. (1990). Poliovirus translation. Curr. Top. Micro. and Imm. 161, 23–47.

Storti, R. V., Scott, M. P., Rich, A., and Pardue, M. L. (1980). Translational control of protein synthesis in response to heat shock in *D. melanogaster* cells. Cell 22, 825–834.

Talmadge, K., and Gilbert, W. (1980). Construction of plasmid vectors with unique Pst1 cloning sites in the signal sequence coding region. Gene 12, 235–241.

Vieira, J., and Messing, J. (1987). Production of single-stranded plasmid DNA. Methods. Enzymol. 153 3.

Winter, J., Wright, R., Duck, N., Gasser, C., Fraley, R., and Shah, D. (1988). The inhibition of petunia HSP70 messenger RNA processing during cadmium chloride stress. Mol. Gen. Genet. 211, 315–319.

Wong, E. Y., Hironaka, C. M., and Fischhoff, D. A. (1992) Plant Mol. Bio. 20, 81–93.

---

I claim:

1. A transformed plant which contains a DNA molecule which comprises:
    (a) a promoter region which functions in plant cells to cause the production of an RNA sequence; which is operably linked to
    (b) a non-translated leader sequence derived from a plant heat shock gene selected from the group consisting of petunia HSP70 gene, soybean HSP17.9 gene, and maize HSP70 gene, wherein said non-translated leader sequence is heterologous to said promoter; which is operably linked to
    (c) a structural DNA sequence, wherein said structural DNA sequence is heterologous to said non-translated leader sequence; which is operably linked to
    (d) a 3' non-translated sequence that functions in plant cells to cause the termination of transcription and the addition of polyadenylated ribonucleotides to the 3' end of the transcribed mRNA sequence.

2. A transformed plant according to claim 1 wherein said promoter region is selected from the group consisting of the FMV promoter region, the CaMV35S promoter region, and the enhanced CaMV35S promoter region.

3. A transformed plant according to claim 1 wherein said structural gene is in the antisense orientation.

4. A transformed plant according to claim 1 wherein said 3' untranslated region is from a gene selected from the group consisting of the nopaline synthase (NOS) gene, the soybean 7S storage protein genes, and the pea small subunit of the ribulose 1,5-bisphosphate carboxylase-oxygenase (ssRUBISCO) E9 gene.

5. A transformed plant according to claim 1 wherein said plant is a dicot.

6. A transformed plant according to claim 1 wherein said plant is a monocot.

* * * * *